United States Patent
Nakanishi et al.

(10) Patent No.: US 8,530,868 B2
(45) Date of Patent: Sep. 10, 2013

(54) ELECTROMAGNETIC RADIATION GENERATING ELEMENT, ELECTROMAGNETIC RADIATION GENERATING DEVICE, AND METHOD OF GENERATING ELECTROMAGNETIC RADIATION

(75) Inventors: Hidetoshi Nakanishi, Kyoto (JP); Masayoshi Tonouchi, Suita (JP)

(73) Assignee: Dainippon Screen Mfg. Co., Ltd., Osaka (JP)

( * ) Notice: Subject to any disclaimer, the term of this patent is extended or adjusted under 35 U.S.C. 154(b) by 0 days.

(21) Appl. No.: 13/621,051

(22) Filed: Sep. 15, 2012

(65) Prior Publication Data

US 2013/0153793 A1 Jun. 20, 2013

(30) Foreign Application Priority Data

Dec. 19, 2011 (JP) ................................. 2011-277033

(51) Int. Cl.
*G01N 21/64* (2006.01)
(52) U.S. Cl.
CPC ....................................... *G01N 21/64* (2013.01)
USPC ..................................................... 250/493.1
(58) Field of Classification Search
USPC .................................. 250/493.1, 459.1, 458.1
See application file for complete search history.

(56) References Cited

U.S. PATENT DOCUMENTS

| | | | |
|---|---|---|---|
| 5,937,118 A * | 8/1999 | Komori | 385/27 |
| 7,990,600 B2 * | 8/2011 | Sachs et al. | 359/241 |
| 2013/0015368 A1 * | 1/2013 | Nakanishi et al. | 250/459.1 |

OTHER PUBLICATIONS

M. Tonouchi, "Current status and future prospects of THz technology" from Applied Physics, p. 160, vol. 75, No. 2 (2006).
K. Serita et al., "Development of Laser Scanning Terahertz Imaging System Using Organic Nonlinear Optical Crystal," Technical Report of the Institute of Electronics, Information, and Communication Engineers, pp. 9-13, vol. 110, No. 66, LQE 2010-3, May 2010.

* cited by examiner

*Primary Examiner* — Kiet T Nguyen
(74) *Attorney, Agent, or Firm* — McDermott Will & Emery LLP

(57) ABSTRACT

An electromagnetic radiation generating device is a device that generates electromagnetic wave pulses from a plane surface. The electromagnetic radiation generating device includes an electromagnetic radiation generating element, a light irradiating unit. The electromagnetic radiation generating element includes: a depletion layer forming body formed by stacking a p-type silicon layer and an n-type silicon layer in a planar pattern; a light receiving surface electrode formed on one surface of the depletion layer forming body, the light receiving surface electrode including a plurality of parallel electrode parts that are equally spaced while a forming distance is maintained between the parallel electrode parts, the forming distance corresponding to the wavelength of the electromagnetic wave pulses generated from the depletion layer forming body; and a rear surface electrode formed on the opposite surface of the depletion layer forming body.

12 Claims, 9 Drawing Sheets

F I G. 1
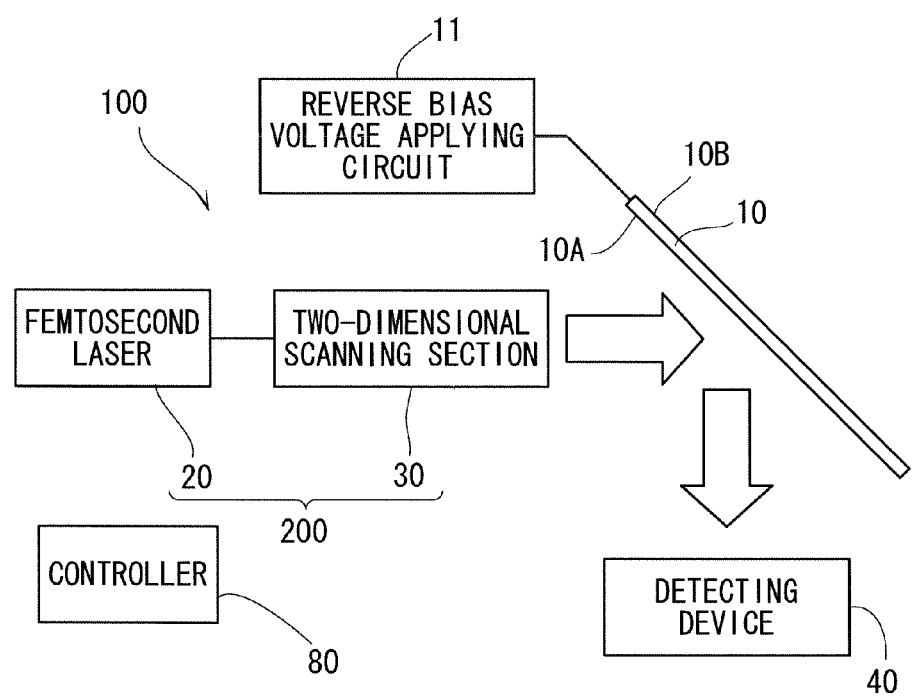

F I G. 5
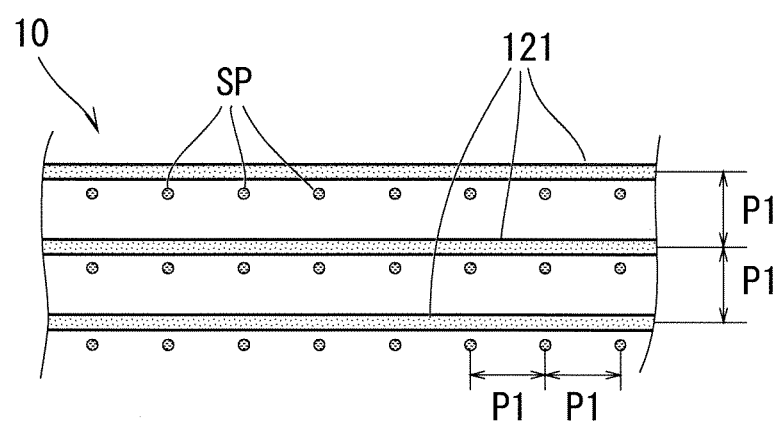

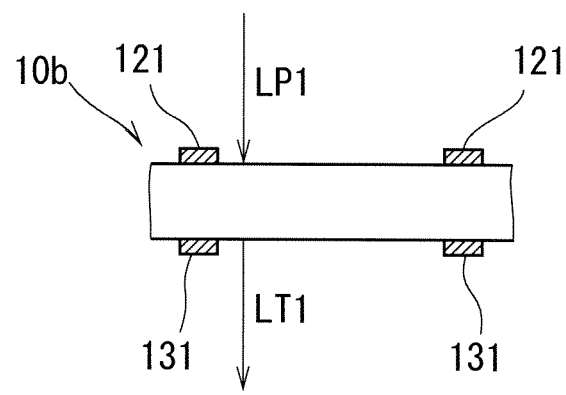
F I G. 9

ELECTROMAGNETIC RADIATION GENERATING ELEMENT, ELECTROMAGNETIC RADIATION GENERATING DEVICE, AND METHOD OF GENERATING ELECTROMAGNETIC RADIATION

BACKGROUND OF THE INVENTION

1. Field of the Invention

The present invention relates to technique of generating electromagnetic radiation in response to received light, and more specifically, to technique of generating electromagnetic radiation from a plane surface.

2. Description of the Background Art

Researches have been made in recent years on technique what is called imaging that forms an image of physical information about a test target by using electromagnetic radiation in a terahertz region (hereinafter also called terahertz wave). A terahertz wave has the properties of both a radio wave and light, and is expected to be applied in industrial purposes for its high performance in passing through an object and in consideration of safety (non-patent literature 1). In the field of security, body scanners already put into practical use and placed for example in air ports use a terahertz wave (mainly a sub-terahertz wave) as a way to pass through an object safely.

Generally, for imaging using a terahertz wave, a test target is caused to move two dimensionally relative to a terahertz wave emitted from an electromagnetic radiation generating element, or the test target is scanned two dimensionally with electromagnetic radiation by using optical technique. In such irradiation with electromagnetic radiation, the test target is scanned relatively with electromagnetic radiation, leading to a complicated device structure. So, technique of generating terahertz waves from a two-dimensional plane surface has already been suggested (non-patent literature 2).

Non-patent literature 2 describes generation of terahertz waves by irradiating DAST crystal being nonlinear optical crystal with femtosecond laser. The DAST crystal is scanned with pulsed light by using a galvanometer mirror, thereby generating terahertz waves from a two-dimensional plane surface.

Non-patent literature 1: "Current status and future prospects of terahertz technology" from Applied Physics, p. 160, Vol. 75, No. 2 (2006), written by Masayoshi Tonouchi Non-patent literature 2: Technical report of the Institute of Electronics, Information, and Communication Engineers, pp. 9-13, vol. 110, No. 66, LQE 2010-3, May, 2010 written by Serita, Tonouchi et al.

However, DAST crystal is a very costly material if it is used as an electromagnetic radiation generating element. Further, large-sized DAST crystal of a size of some millimeters or larger is hard to obtain easily, if manufacture of such DAST crystal is not technically impossible. So, it is in fact difficult to generate electromagnetic radiation from an extensive plane surface by using DAST crystal.

SUMMARY OF THE INVENTION

A first aspect of the present invention is intended for an electromagnetic radiation generating element that generates an electromagnetic wave pulse in response to irradiation with pulsed light. The electromagnetic radiation generating element includes: a depletion layer forming body that forms a depletion layer by stacking a p-type semiconductor layer and an n-type semiconductor layer in a planar pattern; a light receiving surface electrode formed on one surface of the depletion layer forming body, the light receiving surface electrode including a plurality of parallel electrode parts that are equally spaced while a forming distance is maintained between the parallel electrode parts, the forming distance corresponding to the wavelength of the electromagnetic wave pulse generated from the depletion layer forming body; and a rear surface electrode formed on the opposite surface of the depletion layer forming body.

The electromagnetic radiation generating element of the first aspect irradiates the depletion layer extending in a planar pattern with the pulsed light, so that electromagnetic radiation can be generated from a plane surface. Further, the electromagnetic radiation generating element can be made of a relatively inexpensive material, and is allowed to have a large size easily.

Further, the depletion layer can be reverse biased by applying a desired voltage to the light receiving surface electrode and the rear surface electrode holding the depletion layer forming body therebetween. This allows increase of the intensity of electromagnetic radiation to be generated from the depletion layer near the electrode in response to receipt of light. Further, the parallel electrode parts are equally spaced while a distance is maintained therebetween that conforms to the wavelength of electromagnetic radiation to be generated, namely the resolution of the electromagnetic radiation. This allows generation of electromagnetic radiation to conform to resolution specific to electromagnetic radiation, and having a high intensity and a uniform planar pattern.

According to a second aspect of the present invention, the electromagnetic radiation generating element of the first aspect further includes a reverse bias voltage applying circuit that applies a voltage to bring the depletion layer into a reverse biased condition through the light receiving surface electrode and the rear surface electrode.

The electromagnetic radiation generating element of the second aspect is capable of bringing the depletion layer into a reverse biased condition, making it possible to increase the intensity of electromagnetic radiation to be generated.

According to a third aspect of the present invention, in the electromagnetic radiation generating element of the first or second aspect, the light receiving surface electrode further includes a plurality of crossed electrode parts crossing the parallel electrode parts, the crossed electrode parts being equally spaced while a distance in agreement with the forming distance is maintained between the crossed electrode parts.

In the electromagnetic radiation generating element of the third aspect, provision of the crossed electrode parts makes it possible to increase an area adjacent to the electrode. Thus, a point of irradiation with the pulsed light can be designed at a higher degree of flexibility.

According to a fourth aspect of the present invention, in the electromagnetic radiation generating element of any one of the first to third aspects, the rear surface electrode includes a plurality of opposite electrode parts opposite the parallel electrode parts and spaced from each other.

The electromagnetic radiation generating element of the fourth aspect allows electromagnetic radiation generated in the depletion layer in the depletion layer forming body to exit through a space between the opposite electrode parts opposite the light receiving surface.

According to a fifth aspect of the present invention, in the electromagnetic radiation generating element of any one of the first to fourth aspects, the forming distance is from 0.3 mm to 30 mm.

The electromagnetic radiation generating element of the fifth aspect is capable of generating high-intensity electromagnetic radiation in a planar pattern to conform to resolution specific to electromagnetic radiation having a wavelength of from about 0.3 mm to about 30 mm (specifically, electromagnetic radiation having a frequency of from 0.01 THz to 1 THz).

According to a sixth aspect of the present invention, in the electromagnetic radiation generating element of any one of the first to fifth aspects, the forming distance is from 0.6 mm to 3 mm.

The electromagnetic radiation generating element of the sixth aspect is capable of generating high-intensity electromagnetic radiation in a planar pattern to conform to resolution specific to electromagnetic radiation having a wavelength of from 0.6 mm to 3 mm (specifically, electromagnetic radiation having a frequency of from 0.1 THz to 0.5 THz).

A seventh aspect of the present invention is intended for an electromagnetic radiation generating device that generates electromagnetic radiation from a plane surface. The electromagnetic radiation generating device includes an electromagnetic radiation generating element including: a depletion layer forming body that forms a depletion layer by stacking a p-type semiconductor layer and an n-type semiconductor layer in a planar pattern; a light receiving surface electrode formed on one surface of the depletion layer forming body, the light receiving surface electrode including a plurality of parallel electrode parts that are equally spaced while a forming distance is maintained between the parallel electrode parts, the forming distance corresponding to the wavelength of the electromagnetic radiation generated from the depletion layer forming body; and a rear surface electrode formed on the opposite surface of the depletion layer forming body; a light irradiating unit that emits pulsed light toward the electromagnetic radiation generating element; and a reverse bias voltage applying circuit that applies a voltage to bring the depletion layer formed in the depletion layer forming body into a reverse biased condition through the light receiving surface electrode and the rear surface electrode.

The electromagnetic radiation generating device of the seventh aspect irradiates the depletion layer extending in a planar pattern of the electromagnetic radiation generating element with light, so that electromagnetic radiation can be generated from a plane surface. Further, the electromagnetic radiation generating element can be made of a relatively inexpensive material, and is allowed to have a large size easily.

According to an eighth aspect of the present invention, in the electromagnetic radiation generating device of the seventh aspect, the light irradiating unit includes a scanning section that scans the electromagnetic radiation generating element with the pulsed light.

In the electromagnetic radiation generating device of the eighth aspect, the scanning section scans the electromagnetic radiation generating element with the pulsed light. So, electromagnetic radiation can be generated from a plane surface from the electromagnetic radiation generating element.

According to a ninth aspect of the present invention, in the electromagnetic radiation generating device of the eighth aspect, the scanning section applies the pulsed light to points along each of the parallel electrode parts, and applies the pulsed light for a required period of time at intervals in agreement with the forming distance.

The electromagnetic radiation generating device of the ninth aspect is capable of generating electromagnetic radiation from a plane surface so as to conform to the resolution of the electromagnetic radiation.

A tenth aspect of the present invention is intended for a method of generating electromagnetic radiation from a plane surface. The method includes the steps of: (a) emitting pulsed light; and (b) applying the pulsed light to an electromagnetic radiation generating element to generate electromagnetic radiation from a plane surface from the electromagnetic radiation generating element, the electromagnetic radiation generating element including: a depletion layer forming body that forms a depletion layer by stacking a p-type semiconductor layer and an n-type semiconductor layer in a planar pattern; a light receiving surface electrode formed on one surface of the depletion layer forming body; and a rear surface electrode formed on the opposite surface of the depletion layer forming body. The step (b) includes a step (b-1). In the step (b-1), a voltage is applied to bring the depletion layer formed in the depletion layer forming body into a reverse biased condition through the light receiving surface electrode and the rear surface electrode.

The method of the tenth aspect irradiates the depletion layer extending in a planar pattern of the electromagnetic radiation generating element with the pulsed light, so that electromagnetic radiation can be generated from a plane surface. Further, the electromagnetic radiation generating element can be made of a relatively inexpensive material, and is allowed to have a large size easily.

According to an eleventh aspect of the present invention, in the method of the tenth aspect, the step (b) includes a step (b-2). In the step (b-2), the electromagnetic radiation generating element is scanned with the pulsed light.

The method of the eleventh aspect scans the electromagnetic radiation generating element with the pulsed light, so that electromagnetic radiation can be generated efficiently from a plane surface from the electromagnetic radiation generating element.

According to a twelfth aspect of the present invention, in the method of the eleventh aspect, in the step (b-2), the pulsed light is applied to points along each of the parallel electrode parts, and the pulsed light is applied for a required period of time at intervals in agreement with a forming distance corresponding to the wavelength of the electromagnetic radiation generated from the depletion layer forming body.

The method of the twelfth aspect is capable of generating electromagnetic radiation from a plane surface so as to conform to the resolution of the electromagnetic radiation.

Thus, it is an object of the present invention to provide technique capable of generating electromagnetic radiation from a plane surface over a wide area at low cost.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a block diagram showing an electromagnetic radiation generating device and a detecting device;

FIG. 5 is a partial plan view showing a plurality of parallel electrode parts being part of a light receiving surface electrode;

FIG. 9 is a partial side view schematically showing an electromagnetic radiation generating element of a third preferred embodiment.

DESCRIPTION OF THE PREFERRED EMBODIMENTS

Figure 2:
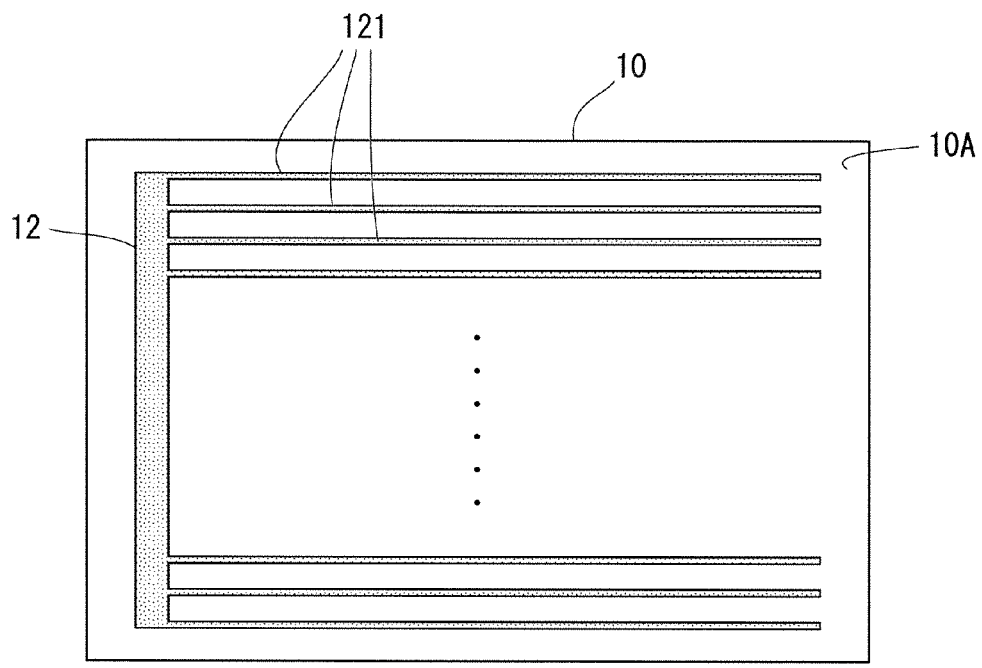
FIG. 2 is a plan view showing a light receiving surface of an electromagnetic radiation generating element.

Preferred embodiments of the present invention are described below by referring to the accompanying drawings. The preferred embodiments described below are exemplary implementations of the present invention and are not intended to limit the technical scope of the present invention.

1. First Preferred Embodiment

<Electromagnetic Radiation Generating Device 100>

FIG. 1 is a block diagram showing an electromagnetic radiation generating device 100 and a detecting device 40. The electromagnetic radiation generating device 100 includes an electromagnetic radiation generating element 10 that generates electromagnetic radiation in response to received light, a femtosecond laser 20 that emits pulsed light, a two-dimensional scanning section 30 that performs two-dimensional scanning with pulsed light, and a controller 80 that controls the operation of the entire electromagnetic radiation generating device 100.

The electromagnetic radiation generating device 100 generates electromagnetic wave pulses mainly in a terahertz region (more specifically, electromagnetic wave pulses in a sub-terahertz region of a frequency band of from 0.01 to 1 THz) in units of planes from the electromagnetic radiation generating element 10 extending in a two-dimensional plane surface. The detecting device 40 detects the intensity of an electromagnetic wave pulse generated in the electromagnetic radiation generating device 100. More specifically, for detection of the intensity of electromagnetic radiation, the detecting device 40 uses terahertz time domain spectroscopy (THz-TDS) or a Schottky barrier diode, for example. The detecting device 40 may have a conventional structure or a structure similar to the conventional structure.

The femtosecond laser 20 is composed of a fiber laser, for example. When the fiber laser is used, the femtosecond laser 20 emits pulsed light LP1 being linearly polarized light having a center wavelength of from about 1 to about 1.5 μm (micrometers), a cycle of from some kilohertz to some hundreds of megahertz, and a pulse width of from about 10 to about 150 fs (femtoseconds). A laser that emits pulsed light in a visible light region or in a near-infrared region having a wavelength of from 400 nm (nanometers) to 1.5 μm (micrometers) is applicable as the femtosecond laser 20. Further, in order to emit pulsed laser of a wavelength of 800 nm from the femtosecond laser 20, a titanium sapphire laser is preferably used as the femtosecond laser 20.

The two-dimensional scanning section 30 is a device that performs two-dimensional scanning of the electromagnetic radiation generating element 10 with the pulsed light LP1 emitted from the femtosecond laser 20. As an example, the two-dimensional scanning section 30 is composed of a galvanometer mirror, a polygon mirror or an acoustooptic modulator, or a combination of these elements. As a result of the two-dimensional scanning performed by the two-dimensional scanning section 30, electromagnetic wave pulses are generated from a plane surface from the electromagnetic radiation generating element 10. In the first preferred embodiment, the femtosecond laser 20 and the two-dimensional scanning section 30 form a light irradiating unit 200 that emits the pulsed light LP1 toward the electromagnetic radiation generating element 10.

<Electromagnetic Radiation Generating Element 10>

Figure 3:
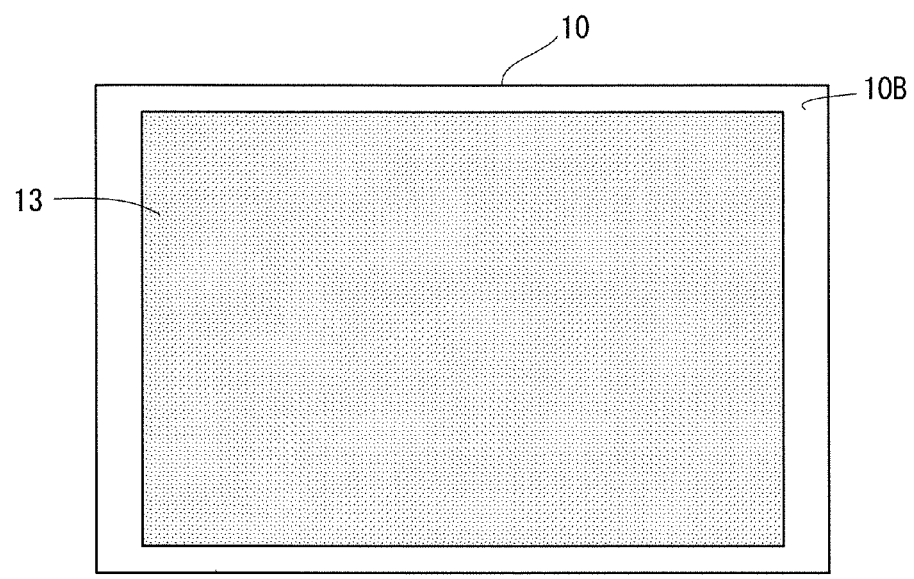
FIG. 3 is a plan view showing a rear surface of the electromagnetic radiation generating element.
Figure 4:
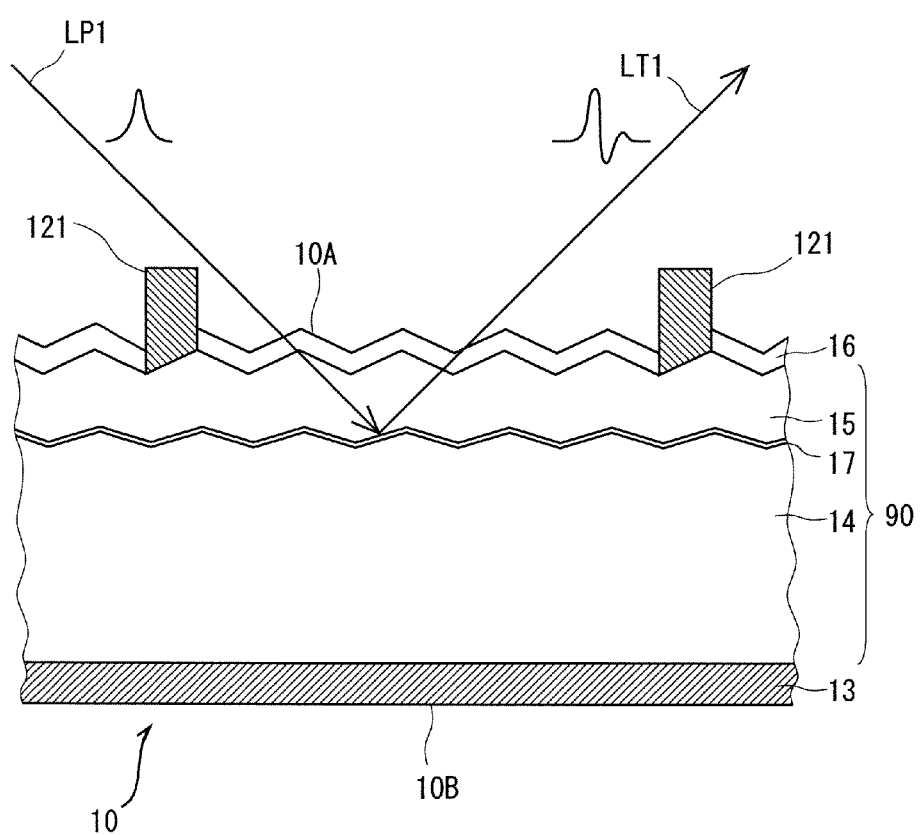
FIG. 4 is a schematic sectional view showing the electromagnetic radiation generating element.

FIG. 2 is a plan view showing a light receiving surface 10A of the electromagnetic radiation generating element 10. FIG. 3 is a plan view showing a rear surface 10B of the electromagnetic radiation generating element 10. FIG. 4 is a schematic sectional view showing the electromagnetic radiation generating element 10.

The electromagnetic radiation generating element 10 is an element formed into a rectangular flat plate. The electromagnetic radiation generating element 10 has the light receiving surface 10A to receive the pulsed light LP1, and the rear surface 10B opposite the light receiving surface 10A. The electromagnetic radiation generating element 10 may be formed into a circular shape (including an oval shape). Further, the electromagnetic radiation generating element 10 may not be a flat element but it may be a curved element.

A light receiving surface electrode 12 is formed on the light receiving surface 10A (see FIG. 2), and a rear surface electrode 13 in the form of a thin film is formed on the rear surface 10B (see FIG. 3). The light receiving surface electrode 12 and the rear surface electrode 13 are composed of aluminum electrodes or transparent electrodes (made of ITO (indium tin oxide) or $SnO_2$ (tin (IV) oxide)), for example.

As shown in FIG. 2, the light receiving surface electrode 12 has a plurality of strip shaped parallel electrode parts 121 arranged in strip shape. The parallel electrode parts 121 are linear members arranged so as to cross a region of the electromagnetic radiation generating element 10 to be irradiated with the pulsed light LP1 (namely, region in which electromagnetic radiation is generated (electromagnetic radiation generation region)). The width of the parallel electrode parts 121 is about 0.2 mm, for example, and this width can be changed where appropriate. Further, the parallel electrode parts 121 are equally spaced while a forming distance P1 is maintained between adjacent ones of the parallel electrode parts 121. The forming distance P1 is described in detail later. All the parallel electrode parts 121 are electrically connected to each other through an electrode part extending in a direction perpendicular to a direction in which the parallel electrode parts 121 extend.

The rear surface electrode 13 is formed entirely on the rear surface 10B of the electromagnetic radiation generating element 10, and occupies at least part facing the parallel electrode parts 121. In the description given below, the direction in which the parallel electrode parts 121 extend may be called a "horizontal direction," and a direction (here, direction in which the parallel electrode parts 121 are arranged in parallel) perpendicular to the "horizontal direction" may be called a "vertical direction."

Further, as shown in FIG. 4, the electromagnetic radiation generating element 10 has a stacked structure including the rear surface electrode 13, a p-type silicon layer 14, an n-type silicon layer 15, and an antireflection film 16 stacked in a planar pattern and placed one above the other in this order as viewed from the rear surface 10B. The p-type silicon layer 14 is an example of a p-type semiconductor, and the n-type silicon layer 15 is an example of an n-type semiconductor. Single-crystalline silicon, polycrystalline silicon, or amorphous silicon generally used in devices such as solar cells is preferably used to form the p-type and n-type silicon layers 14 and 15. Silicon oxide or silicon nitride is preferably used to form the antireflection film 16, for example.

A junction between the p-type and n-type silicon layers 14 and 15 is a pn junction 17 in which a depletion layer extending in a two-dimensional plane surface is formed. In the pn junction 17, electrons and positive holes diffuse and combine with each other to generate diffusion current. As a result, the depletion layer that does not include many electrons and positive holes is formed near the pn junction 17. So, a stacked structure with the p-type and n-type silicon layers 14 and 15 forms a depletion layer forming body 90. Or, the depletion layer forming body may be formed by placing an intrinsic semiconductor layer between the p-type and n-type silicon layers 14 and 15, namely, by preparing a pin junction.

In the deletion layer, forces acting to pull electrons and positive holes back to n and p regions respectively are generated to generate an electric field (internal electric field) inside the depletion layer. If light of energy higher than that of a band gap is applied to the pn junction, photoelectrons are caused to move toward the n-type semiconductor by the internal electric field, and positive holes left in the pn junction move to the p-type semiconductor. In a photo device such as a solar cell, for example, movement of photoelectrons is taken to the outside through electrodes attached to the n-type and p-type semiconductors. Thus, in the photo device, movements of free electrons and free positive holes occur in response to irradiation of the depletion layer in the pn junction with light, and these movements are used as DC power.

In response to irradiation of the depletion layer being a photo-excited carrier generating region with the pulsed light LP1, photo-excited carriers are accelerated by the internal electric field to move, thereby generating pulsed current. If the current changes with time, electromagnetic radiation is generated according to Maxwell's equations. To be specific, in response to irradiation of the electromagnetic radiation generating element 10 with the pulsed light LP1, an electromagnetic pulse is generated from part of the deletion layer having received pulsed light. As an example, in response to irradiation of the electromagnetic radiation generating element 10 with pulsed light in a wavelength range of from that of visible light (400 nm) to that of near-infrared light (1.5 μm), an electromagnetic wave pulse (hereinafter also called an electromagnetic wave pulse LT1) mainly covering a frequency band of from 0.01 THz to 1 THz is generated.

The light receiving surface 10A of the electromagnetic radiation generating element 10 has the shape of desired texture intended to suppress loss of light reflection. More specifically, as shown in FIG. 4, the light receiving surface 10A is given projections and recesses of some micrometers to some tens of micrometers formed by anisotropic etching, or V-shaped slots formed by mechanical technique, for example. As a result, the light receiving surface 10A of the electromagnetic radiation generating element 10 is given a structure that lets light in efficiently. Thus, the emitted pulsed light LP1 of a predetermined wavelength can easily reach the pn junction 17. As an example, if the pulsed light LP1 is visible light of a wavelength of from 400 nm to 1 μm, the pulsed light LP1 reaches the pn junction 17 easily.

The two-dimensional scanning section 30 makes the pulsed light LP1 enter the light receiving surface 10A of the electromagnetic radiation generating element 10 in such a manner that the optical axis of the pulsed light LP1 is at an angle relative to the light receiving surface 10A. In the first preferred embodiment, an angle of irradiation is determined such that the incident angle of the pulsed light LP1 becomes 45 degrees. However, the incident angle is not limited to 45 degrees, but it can be changed where appropriate in a range of from zero to 90 degrees. Many of the electromagnetic wave pulses LT1 generated from the electromagnetic radiation generating element 10 are allowed to reflect off the rear surface electrode 13 if the rear surface electrode 13 is a transparent electrode made of $SnO_2$ or ITO. In this case, by causing the pulsed light LP1 to enter the light receiving surface 10A at right angles, the electromagnetic wave pulse LT1 having reflected off the rear surface electrode 13 can travel toward the light receiving surface 10A.

The controller 80 has a generally employed structure of a computer including a CPU, a ROM and a RAM, for example. The controller 80 expands a program stored in a storage section (including a storage such as a hard disk drive, a portable medium such as a CD-ROM, and a RAM storing information temporarily) on the RAM and executes the program, thereby controlling the operations of the constituting elements of the electromagnetic radiation generating device 100 (including the femtosecond laser 20, the two-dimensional scanning section 30, a reverse bias voltage applying circuit 11, and others). However, some of the constituting elements of the electromagnetic radiation generating device 100 may be controlled manually.

As shown in FIG. 1, the reverse bias voltage applying circuit 11 is connected to the electromagnetic radiation generating element 10. The reverse bias voltage applying circuit 11 includes a DC power supply (not shown in the drawings), and applies a voltage to bring the depletion layer into a reverse biased condition through the light receiving surface electrode 12 and the rear surface electrode 13. Preferably, the reverse bias voltage applying circuit 11 applies a voltage of from 5 to 10 V.

Bringing the depletion layer into a reverse biased condition increases the electric field of the depletion layer. So, more photo-excited carriers are allowed to move in response to irradiation with the pulsed light LP1, making it possible to relatively increase the intensity of the electric field of an electromagnetic wave pulse to be generated. In the depletion layer, an electric field increases in part as the part is closer to the parallel electrode parts 121. So, the intensity of an electromagnetic wave pulse to be generated becomes higher in this part. As a result, by bringing the depletion layer into a reverse biased condition, the electromagnetic radiation generating element 10 is allowed to generate electromagnetic radiation of substantially the same intensity as that of electromagnetic radiation generated from a conventional terahertz wave generating element (such as a photoconductive switch).

Figure 6:
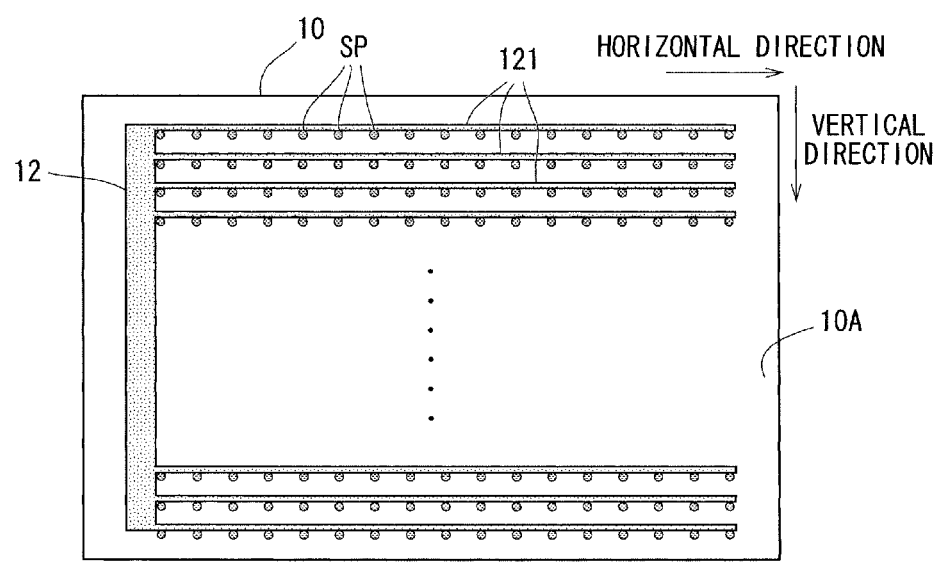
FIG. 6 is a plan view showing the light receiving surface of the electromagnetic radiation generating element.

FIG. 5 is a partial plan view showing the parallel electrode parts 121 being part of the light receiving surface electrode 12. FIG. 6 is a plan view showing the light receiving surface 10A of the electromagnetic radiation generating element 10. Points irradiated with the pulsed light LP1 are shown in FIG. 6. As described above, the parallel electrode parts 121 are equally spaced while the required forming distance P1 is maintained between adjacent ones of the parallel electrode parts 121. The forming distance P1 corresponds to the wavelength of the electromagnetic wave pulse LT1 generated from the electromagnetic radiation generating element 10 in response to irradiation with the pulsed light LP1. Here, a "distance corresponding to the wavelength of an electromagnetic wave pulse to be generated" is a distance in agreement with a particular wavelength in a wavelength region of electromagnetic radiation generated in the depletion layer of the electromagnetic radiation generating element 10.

As an example, the electromagnetic radiation generating element 10 of the first preferred embodiment generates an electromagnetic wave pulse mainly in a range of from 0.01 to 1 THz as described above. A wavelength region in this case is mainly from about 0.3 mm to about 30 mm. So, the value of the forming distance P1 is selected from this range. In the first preferred embodiment, an electromagnetic wave pulse generated from the electromagnetic radiation generating element 10 has an intensity that becomes highest at a frequency of about 0.1 THz (wavelength of about 3 mm) in a frequency region thereof. So, if an electromagnetic wave pulse at this frequency is mainly used, the forming distance P1 is desirably set at 3 mm. Electromagnetic radiation in a terahertz band of from 0.1 THz to 30 THz functions as a light wave traveling in a straight line and a radio wave passing through an object. Meanwhile, a more preferable frequency band thereof is from 0.1 THz to 0.5 THz (wavelength of from about 0.6 mm to about 3 mm). So, if an electromagnetic wave pulse in this frequency band is used, it is desirable that the forming distance P1 fall within a range of from 0.6 mm to 3 mm.

The forming distance P1 between the parallel electrode parts 121 is made to agree with the wavelength of the electromagnetic wave pulse LT1 for the following reason. The electromagnetic wave pulses LT1 are generated from a plane surface in the first preferred embodiment. Meanwhile, the resolution of each electromagnetic wave pulses LT1 depends on the wavelength of the electromagnetic wave pulse LT1. So, generating the electromagnetic wave pulses LT1 at intervals shorter than the wavelength thereof brings about substantially no significance to the detecting device 40 in terms of resolution. In contrast, in the first preferred embodiment, the pulsed light LP1 is applied to points near the parallel electrode parts 121 to form spots (laser spots SP) as shown in FIG. 5, thereby generating the electromagnetic wave pulses LT1 of a high intensity from the depletion layer in a reverse biased condition. Making the forming distance between the parallel electrode parts 121 shorter than the wavelength of the electromagnetic wave pulse LT1 to be generated entails cost such as material cost higher than necessary, and at the same time, reduces an area capable of being irradiated with the pulsed light LP1.

So, the forming distance P1 between the parallel electrode parts 121 is made to conform to the wavelength of the electromagnetic wave pulse LT1. This allows conformance to the resolution of the electromagnetic wave pulses LT1 to be generated from a plane surface, and at the same time, reduces cost required for formation of the parallel electrode parts 121. This also makes it possible to keep a wide area for irradiation with the pulsed light LP1, so that irradiation with the pulsed light LP1 can be controlled easily.

As shown in FIG. 5, the two-dimensional scanning section 30 applies the pulsed light LP1 to one irradiation point (point corresponding to a laser spot SP) for a given period of time. After this irradiation is finished, the two-dimensional scanning section 30 turns to a next point shifted by a length in agreement with the forming distance P1 in the horizontal direction, and applies the pulsed light LP1 to this point to form a next laser spot SP. By repeating this process, the two-dimensional scanning section 30 performs horizontal scanning with the pulsed light LP1 along one parallel electrode part 121. As a result, points along one parallel electrode part 121 are irradiated with the pulsed light LP1.

After irradiation with the pulsed light LP1 along one parallel electrode part 121 is finished, the two-dimensional scanning section 30 turns to a point shifted by a length in agreement with the forming distance P1 in the vertical direction to perform horizontal scanning with the pulsed light LP1 along an adjacent parallel electrode part 121. To be specific, the two-dimensional scanning section 30 performs horizontal scanning with the pulsed light LP1 and makes a shift in the vertical direction repeatedly, thereby applying the pulsed light LP1 to points along all the parallel electrode parts 121 as shown in FIG. 6. As a result, the electromagnetic wave pulses LT1 are generated in the form of lattice points spaced by the forming distance P1 in each of the vertical and horizontal directions. As a result, the electromagnetic wave pulses LT1 are emitted from a plane surface from the electromagnetic radiation generating element 10.

The p-type or n-type silicon layer 14 or 15 has a uniform crystal structure if the p-type or n-type silicon layer 14 or 15 is made of single-crystalline silicon. In this case, variations in the intensity of the electromagnetic wave pulses LT1 generated at corresponding points of the electromagnetic radiation generating element 10 can be made small. In contrast, if the p-type and n-type silicon layers 14 and 15 are made of polycrystalline silicon, the intensity of the electromagnetic wave pulses LT1 to be generated may be changed slightly depending on the condition of crystal. In response, an optical modulating element such as a GLV (grating light valve) may be provided to the two-dimensional scanning section 30. The optical modulating element controls the intensity of the pulsed light LP1 at each point on the electromagnetic radiation generating element 10, so that the electromagnetic wave pulses LT1 generated at corresponding points of the electromagnetic radiation generating element 10 are allowed to have a uniform intensity.

<Flow of Generation of Electromagnetic Wave Pulse>

Figure 7:
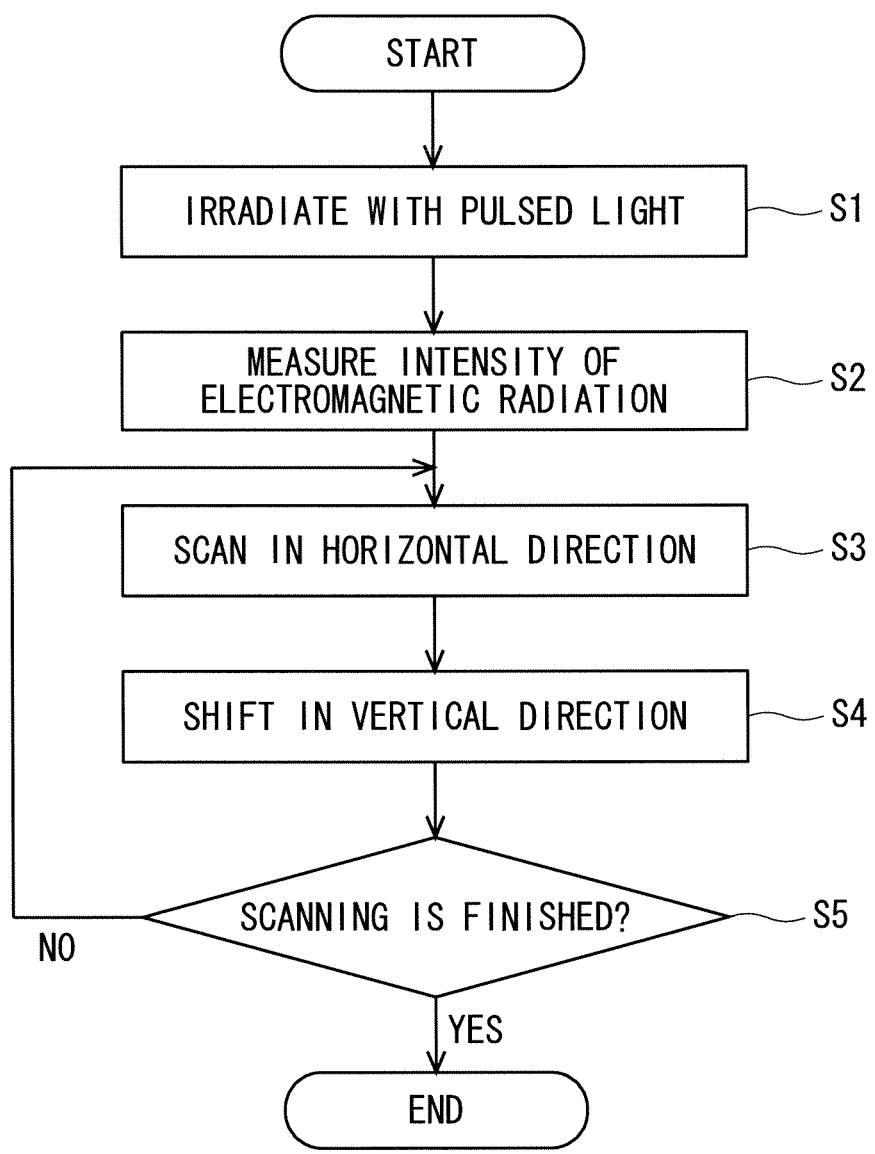
FIG. 7 is a flow diagram showing a flow of generation of an electromagnetic wave pulse in the electromagnetic radiation generating device.

A flow of generation of an electromagnetic wave pulse is described next by referring to FIG. 7. The following flow of generation of an electromagnetic wave pulse is described as an example, and can be changed where appropriate FIG. 7 is a flow diagram showing the flow of generation of the electromagnetic wave pulse LT1 in the electromagnetic radiation generating device 100. The electromagnetic radiation generating element 10 is installed in advance in the electromagnetic radiation generating device 100. Further, the reverse bias voltage applying circuit 11 applies a required voltage to the electromagnetic radiation generating element 10 to bring the depletion layer into a reverse biased condition. In this state, irradiation of the electromagnetic radiation generating element 10 with the pulsed light LP1 is started (step S1).

In step S1, the pulsed light LP1 is applied to an arbitrary point near the parallel electrode parts 121. Then, the detecting device 40 detects the intensity of the electromagnetic wave pulse LT1 emitted from the electromagnetic radiation generating device 100 (step S2). Step S2 is intended to see if the emitted electromagnetic wave pulse LT1 has an intensity exceeding a desired intensity. If the intensity of the electromagnetic wave pulse LT1 is not sufficient, a voltage applied by the reverse bias voltage applying circuit 11 is controlled, or the intensity of the pulsed light LP1 is increased, where appropriate.

Next, the two-dimensional scanning section 30 scans the electromagnetic radiation generating element 10 with the pulsed light LP1. More specifically, as described by referring to FIG. 5, the two-dimensional scanning section 30 starts to apply the pulsed light LP1 from one end of one parallel electrode part 121, and continues to apply the pulsed light LP1 while shifting the pulsed light LP1 in the horizontal direction by the forming distance P1 until the pulsed light LP1 reaches the opposite end of the parallel electrode part 121, thereby realizing horizontal scanning with the pulsed light LP1 along the parallel electrode part 121 (step S3).

When the pulsed light LP1 for the horizontal scanning reaches the opposite end of the parallel electrode part 121, the two-dimensional scanning section 30 shifts the pulsed light LP1 in the vertical direction by a distance in agreement with the forming distance P1 (step S4). This changes a point to be irradiated with the pulsed light LP1 to a point near an adjacent parallel electrode part 121 in the vertical direction. Then, it is determined if horizontal scanning is required further (step S5). In step S5, the determination is made by the controller 80 that controls the two-dimensional scanning section 30.

If it is determined that horizontal scanning is required (NO in step S5), the flow returns to step S3 where the two-dimensional scanning section 30 performs horizontal scanning. If it is determined that horizontal scanning is not required (YES in step S5), the two-dimensional scanning section 30 finishes its operation. As described above, the two-dimensional scanning section 30 repeats steps S3 to S5 to generate the electromagnetic wave pulses LT1 in units of planes from the electromagnetic radiation generating element 10.

As described above, the electromagnetic radiation generating element 10 generates electromagnetic radiation from the depletion layer from the stacked structure with the p-type and n-type semiconductor layers, and is capable of using conventional technique of manufacturing photo devices such as solar cells. This makes manufacturing cost relatively low, while making it possible to form the large-sized electromagnetic radiation generating element 10 easily. Thus, the electromagnetic radiation generating device 100 is capable of generating electromagnetic radiation from a plane surface over a wide area at low cost.

2. Second Preferred Embodiment

Figure 8:
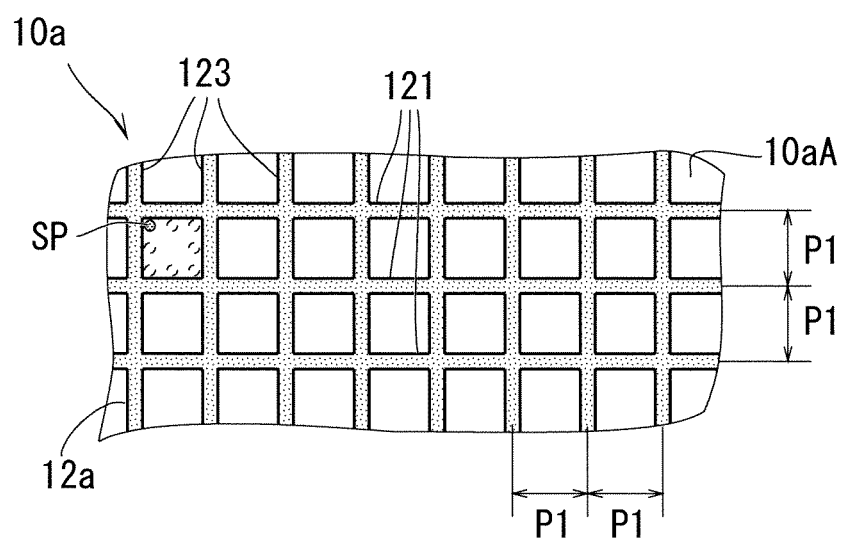
FIG. 8 is a partial plan view showing a light receiving surface of an electromagnetic radiation generating element of a second preferred embodiment.

FIG. 8 is a partial plan view showing a light receiving surface 10aA of an electromagnetic radiation generating element 10a of a second preferred embodiment. In the description given below, elements having the same functions as those of corresponding elements of the first preferred embodiment are identified by the same reference numbers, and will not be described again.

A light receiving surface electrode 12a is formed on the light receiving surface 10aA of the electromagnetic radiation generating element 10a of the second preferred embodiment. The light receiving surface electrode 12a includes a plurality of parallel electrode parts 121 arranged in parallel and equally spaced in the vertical direction with a forming distance P1 maintained between the parallel electrode parts 121, and a plurality of crossed electrode parts 123 extending in a direction (here, vertical direction) perpendicular to a direction in which the parallel electrode parts 121 extend. The crossed electrode parts 123 are equally spaced while a distance in agreement with the forming distance P1 between the parallel electrode parts 121 is maintained between the crossed electrode parts 123.

Provision of the crossed electrode parts 123 makes it possible to increase an area adjacent to the electrode on the light receiving surface 10aA. Thus, a point of irradiation with pulsed light LP1 applied to obtain a high-intensity electromagnetic wave pulse LT1 (point of a laser spot SP) can be designed at a higher degree of flexibility.

A distance between adjacent ones of the crossed electrode parts 123 is not necessarily required to agree with the forming distance P1. However, in order to generate electromagnetic wave pulses LT1 of a uniform intensity from a plane surface, it is desirable that the crossed electrode parts 123 be equally spaced while a distance therebetween is in agreement with intervals of irradiation with the pulsed light LP1 (here, forming distance P1).

3. Third Preferred Embodiment

FIG. 9 is a partial side view schematically showing an electromagnetic radiation generating element 10b of a third preferred embodiment. In the third preferred embodiment, a rear surface electrode 13b includes a plurality of opposite electrode parts 131. The opposite electrode parts 131 are provided at positions opposite parallel electrode parts 121, and are spaced from each other. Although not shown in the drawings, the opposite electrode parts 131 are electrically connected to each other through an electrode part provided in a difference position.

The opposite electrode parts 131 are formed such that a distance between adjacent ones of the opposite electrode parts 131 agrees with a forming distance P1 between the parallel electrode parts 121. So, if pulsed light LP1 enters a light receiving surface of the electromagnetic radiation generating element 10b at right angles through a position near the parallel electrode part 121 as shown in FIG. 9, an electromagnetic wave pulse LT1 can be emitted through a space between the adjacent opposite electrode parts 131 on a rear surface 10Bb opposite the light receiving surface. A distance between the adjacent opposite electrode parts 131 is not necessarily required to agree with the forming distance P1, but it can be changed where appropriate.

4. Modifications

The present invention is not limited to the preferred embodiments described above, but various modifications thereof can be devised.

As an example, in the aforementioned preferred embodiments, the two-dimensional scanning section 30 applies the pulsed light LP1 sequentially in a direction in which each of the parallel electrode parts 121 extends. Alternatively, the two-dimensional scanning section 30 may apply the pulsed light LP1 sequentially in a direction in which the parallel electrode parts 121 are arranged.

The electromagnetic radiation generating element 10 of the aforementioned preferred embodiments is a reflection-type electromagnetic radiation generating element where the pulsed light LP1 enters the light receiving surface 10A on which the parallel electrode parts 121 are formed, and the electromagnetic wave pulse LT1 to be used is emitted from the same light receiving surface 10A. However, the electromagnetic radiation generating element 10 may be a transmission-type electromagnetic radiation generating element. In this case, the pulsed light LP1 is applied to part in which the parallel electrode parts 121 are formed through the rear surface 10B. It is preferable that the pulsed light LP1 have a wavelength in a range of from 1 to 1.5 μm that allows the pulsed light LP1 to pass through silicon at a high rate. Meanwhile, the wavelength of the pulsed light LP1 may alternatively be 800 nm. In this case, a transparent electrode is used as the rear surface electrode 13.

The preferred embodiments of the present invention can be combined freely, and each of the preferred embodiments can be modified or omitted where appropriate as long as no contradiction is generated therebetween.

While the invention has been shown and described in detail, the foregoing description is in all aspects illustrative and not restrictive. It is therefore understood that numerous modifications and variations can be devised without departing from the scope of the invention.

What is claimed is:

1. An electromagnetic radiation generating element that generates an electromagnetic wave pulse in response to irradiation with pulsed light, the electromagnetic radiation generating element comprising:

a depletion layer forming body that forms a depletion layer by stacking a p-type semiconductor layer and an n-type semiconductor layer in a planar pattern;

a light receiving surface electrode formed on one surface of said depletion layer forming body, the light receiving surface electrode including a plurality of parallel electrode parts that are equally spaced while a forming distance is maintained between the parallel electrode parts, the forming distance corresponding to the wavelength of said electromagnetic wave pulse generated from said depletion layer forming body; and a rear surface electrode formed on the opposite surface of said depletion layer forming body.

2. The electromagnetic radiation generating element according to claim 1, further comprising a reverse bias voltage applying circuit that applies a voltage to bring said depletion layer into a reverse biased condition through said light receiving surface electrode and said rear surface electrode.

3. The electromagnetic radiation generating element according to claim 1, wherein said light receiving surface electrode includes a plurality of crossed electrode parts crossing said parallel electrode parts, the crossed electrode parts being equally spaced while a distance in agreement with said forming distance is maintained between the crossed electrode parts.

4. The electromagnetic radiation generating element according to claim 1, wherein said rear surface electrode includes a plurality of opposite electrode parts opposite said parallel electrode parts and spaced from each other.

5. The electromagnetic radiation generating element according to claim 1, wherein said forming distance is from 0.3 mm to 30 mm.

6. The electromagnetic radiation generating element according to claim 1, wherein said forming distance is from 0.6 mm to 3 mm.

7. An electromagnetic radiation generating device that generates electromagnetic radiation from a plane surface, comprising:

an electromagnetic radiation generating element including: a depletion layer forming body that forms a depletion layer by stacking a p-type semiconductor layer and an n-type semiconductor layer in a planar pattern; a light receiving surface electrode formed on one surface of said depletion layer forming body, the light receiving surface electrode including a plurality of parallel electrode parts that are equally spaced while a forming distance is maintained between the parallel electrode parts, the forming distance corresponding to the wavelength of said electromagnetic radiation generated from said depletion layer forming body; and a rear surface electrode formed on the opposite surface of said depletion layer forming body;

a light irradiating unit that emits pulsed light toward said electromagnetic radiation generating element; and a reverse bias voltage applying circuit that applies a voltage to bring said depletion layer formed in said depletion layer forming body into a reverse biased condition through said light receiving surface electrode and said rear surface electrode.

8. The electromagnetic radiation generating device according to claim 7, wherein said light irradiating unit includes a scanning section that scans said electromagnetic radiation generating element with said pulsed light.

9. The electromagnetic radiation generating device according to claim 8, wherein said scanning section applies said pulsed light to points along each of said parallel electrode parts, and applies said pulsed light for a required period of time at intervals in agreement with said forming distance.

10. A method of generating electromagnetic radiation from a plane surface, comprising the steps of:

(a) emitting pulsed light; and (b) applying said pulsed light to an electromagnetic radiation generating element to generate electromagnetic radiation from a plane surface from the electromagnetic radiation generating element, the electromagnetic radiation generating element including: a depletion layer forming body that forms a depletion layer by stacking a p-type semiconductor layer and an n-type semiconductor layer in a planar pattern; a light receiving surface electrode formed on one surface of said depletion layer forming body; and a rear surface electrode formed on the opposite surface of said depletion layer forming body, said step (b) including the step of (b-1) applying a voltage to bring said depletion layer formed in said depletion layer forming body into a reverse biased condition through said light receiving surface electrode and said rear surface electrode.

11. The method according to claim 10, wherein said step (b) includes the step of (b-2) scanning said electromagnetic radiation generating element with said pulsed light.

12. The method according to claim 11, wherein:

the light receiving surface electrode includes a plurality of parallel electrode parts that are equally spaced while a forming distance is maintained between the parallel electrode parts, and in said step (b-2), said pulsed light is applied to points along each of said parallel electrode parts, and said pulsed light is applied for a required period of time at intervals in agreement with a forming distance corresponding to the wavelength of said electromagnetic radiation generated from said depletion layer forming body.

* * * * *

UNITED STATES PATENT AND TRADEMARK OFFICE
CERTIFICATE OF CORRECTION

PATENT NO. : 8,530,868 B2  
APPLICATION NO. : 13/621051  
DATED : September 10, 2013  
INVENTOR(S) : Hidetoshi Nakanishi et al.

Page 1 of 1

It is certified that error appears in the above-identified patent and that said Letters Patent is hereby corrected as shown below:

On the Title Page

In item "(73) Assignee", Assignees should read --Dainippon Screen Mfg. Co., Ltd, Kyoto (JP) and Osaka University, Osaka (JP)-- rather than "Dainippon Screen Mfg. Co., Ltd. Osaka (JP)"

Signed and Sealed this  
Eighteenth Day of November, 2014

Michelle K. Lee  
*Deputy Director of the United States Patent and Trademark Office*